United States Patent
Feenstra et al.

(10) Patent No.: US 6,780,864 B1
(45) Date of Patent: Aug. 24, 2004

(54) PIPERAZINE AND PIPERIDINE COMPOUNDS

(75) Inventors: Roelof Feenstra, Weesp (NL); Johannes A. M. Van Der Heijden, Weesp (NL); Cornelis G. Kruse, Weesp (NL); Stephen K. Long, Weesp (NL); Johannes Mos, Weesp (NL); Gerben M. Visser, Weesp (NL); Gustaaf J. M. Van Scharrenburg, Weesp (NL); Gerrit P. Toorop, deceased, late of Weesp (NL), by Anne G. Toorop, heiress

(73) Assignee: DUPHAR International Research BV, Weesp (NL)

( * ) Notice: Subject to any disclaimer, the term of this patent is extended or adjusted under 35 U.S.C. 154(b) by 0 days.

(21) Appl. No.: 09/831,149

(22) PCT Filed: Nov. 10, 1999

(86) PCT No.: PCT/EP99/08702

§ 371 (c)(1),
(2), (4) Date: Aug. 14, 2001

(87) PCT Pub. No.: WO00/29397

PCT Pub. Date: May 25, 2000

(30) Foreign Application Priority Data

Nov. 13, 1998 (EP) .............................. 98203871

(51) Int. Cl.$^7$ .................. C07D 263/58; C07D 413/04; C07D 277/68; A61K 31/42; A61K 31/40

(52) U.S. Cl. .................. 514/254.02; 544/367; 546/209; 514/321

(58) Field of Search .................... 544/367; 514/254.02, 514/321; 546/209

(56) References Cited

U.S. PATENT DOCUMENTS 4,737,505 A    4/1988 Guillaume et al. ......... 514/323

FOREIGN PATENT DOCUMENTS

| EP | 0 169 148 A1 | 1/1986 |
| EP | 0190 472 A1 * | 6/1986 |
| EP | 0 189 612 A1 | 8/1986 |
| EP | 0 900 792 A1 | 3/1999 |
| WO | WO 94/13659 | 6/1994 |
| WO | WO 95/33721 | 12/1995 |
| WO | WO 96/03400 | 2/1996 |
| WO | WO 97/36893 | 10/1997 |

* cited by examiner

Primary Examiner—Richard Raymond
Assistant Examiner—Hong Liu
(74) Attorney, Agent, or Firm—Finnegan, Henderson, Farabow, Garrett & Dunner, LLP

(57) ABSTRACT

The invention relates to a group of novel piperazine and piperidine derivatives of formula (I), wherein: $S_1$ is hydrogen, halogen, alkyl (1–3C), CN, $CF_3$, $OCF_3$, $SCF_3$, alkoxy (1–3C), amino or mono- or dialkyl (1–3C) substituted amino, or hydroxy; X represents $NR_3$, S, $CH_2$, O, SO or $SO_2$, wherein $R_3$ is H or alkyl (1–3C); . . . Z represents =C or —N; —$R_1$ independently represent H or alkyl (1–3C), or $R_1$ and $R_2$ together can form a bridge 2 or 3 C-atoms; $R_4$ is hydrogen or alkyl (1–3C); Q is methyl, ethyl, ethyl substituted with one or more fluorine atoms, cyclopropyl—methyl, optionally substituted with one or more fluorine atoms, and salts and prodrugs thereof. It has been found that these compounds have both partial dopamine $D_2$-receptor agonism and partial serotonin 5-$HT_{1A}$-receptor agonism mediated activities.

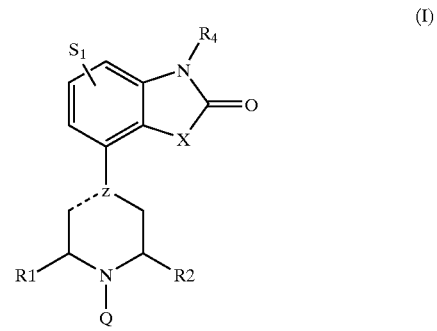

(I)

13 Claims, No Drawings

PIPERAZINE AND PIPERIDINE COMPOUNDS

The present invention relates to a new group of piperazine and di-dehydropiperidine derivatives having interesting pharmacological properties due to a combination of both partial dopamine $D_2$-receptor agonism and partial serotonin 5-$HT_{1A}$-receptor agonism mediated activities. In addition, affinity for adrenergic $\alpha_1$-receptors is present It is known from EP 0189612 that piperazine derivatives substituted at one nitrogen with a phenyl-heterocyclic group, and unsubstituted at the other nitrogen atom, have psychotropic activity.

Further it is known from EP 0190472 that benzofuran- and benzodioxole-piperazine derivatives substituted at the other nitrogen atom of the piperazine group, have also psychotropic activity.

Finally it is known from EP 0169148 that 1,3-dihydro-4-(1-ethyl-1,2,3,6-tetrahydropyridin-4-yl)-2H-indol-2-one and similar compounds have analgetic properties.

It has now surprisingly been found that a small group of piperazine and piperidine derivatives having formula (I)

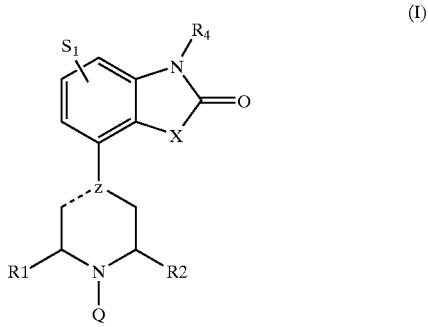

(I)

wherein
- $S_1$ is hydrogen, halogen, alkyl (1-3C), CN, $CF_3$, $OCF_3$, $SCF_3$, alkoxy (1-3C), amino or mono- or dialkyl (1-3C) substituted amino, or hydroxy,
- X represents $NR_3$, S, $CH_2$, O, SO or $SO_2$, wherein $R_3$ is H or alkyl (1-3C),
- ... Z represents =C or —N,
- $R_1$ and $R_2$ independently represent H or alkyl (1-3C), or $R_1$ and $R_2$ together can form a bridge of 2 or 3 C-atoms,
- $R_4$ is hydrogen or alkyl (1-3C),
- Q is methyl, ethyl, ethyl substited with one or more fluorine atoms, cyclopropyl—methyl, optionally substituted with one or more fluorine atoms, with the proviso that when $S_1$, $R_1$, $R_2$ and $R_4$ are hydrogen, ... Z is =C and Q is ethyl, X cannot represent $CH_2$, and salts and prodrugs thereof have a combination of partial dopamine $D_2$-receptor agonism and partial serotonin 5-$HT_{1A}$-receptor agonism activities.

Preferred compounds according to the invention are compounds of the formula (I) wherein $S_1$, $R_1$, $R_2$ and $R_4$ are hydrogen, X represents oxygen, and ... Z and Q have the above meanings, and the salts thereof.

Especially preferred are the compounds wherein $S_1$, $R_1$, $R_2$ and $R_4$ are hydrogen, X is oxygen, ... Z represents —N and Q is methyl or ethyl and salts thereof. The most preferred compound being the one wherein Q is methyl.

Compounds according to the invention show affinities for both the dopamine $D_2$ receptor (pKi range 7.5–8.5) and the serotonin 5-$HT_{1A}$ receptor (pKi range 7.0–8.0) measured according to well-defined methods (e.g.: Creese I, Schneider R and Snyder S H, [$^3$H]Spiroperidol labels dopamine receptors in rat pituitary and brain, *Eur J Pharmacol* 1997, 46: 377–381 and Gozlan H, E I Mestikawy S, Pichat L, Glowinsky J and Hamon M, 1983, Identification of presynaptic serotonin autoreceptors using a new ligand $^3$H-PAT, *Nature* 1983, 305:140–142).

The compounds show varying activities as partial agonists at the dopamine $D_2$ receptor and, surprisingly, at the 5-$HT_{1A}$ receptor. This activity was measured on the formation of adenylate cyclase in cell-lines expressing these cloned receptors (e.g. human $D_2$ receptors and 5-$HT_{1A}$ receptors expressed in CHO cell line according to the methods described by Solomon Y, Landos C, Rodbell M, 1974, A highly selective adenylyl cyclase assay, *Anal Biochem* 1974, 58: 541–548 and Weiss S, Sebben M and Bockaert J J, 1985, Corticotropin-peptide regulation of intracellular cyclic AMP production in cortical neurons in primary culture, *J Neurochem* 1985, 45:869–874).

The unique combination of both partial dopamine $D_2$-receptor agonism and partial serotonin 5-$HT_{1A}$-receptor agonism results in a surprisingly broad activity in several animal models, predictive for psychiatric and/or neurologic disturbances.

The compounds show a surprisingly high efficacy in a therapeutic model for anxiolytic/antidepressant activity: the conditioned ultrasonic vocalization model in rats (see e.g.: Molewijk H E, Van der Poel A M, Mos J, Van der Heyden J A M and Olivier B (1995), Conditioned ultrasonic vocalizations in adult male rats as a paradigm for screening anti-panic drugs, *Psychopharmacology* 1995, 117: 32–40). The activity of the compounds in this model was in the low microgram/kg range, which is surprisingly more active (by a factor 100 to 3000) compared to the compounds previously described in EP 0190472 and EP 0398413.

In addition these compounds also show effects in models predictive for antidepressant activity at higher doses (forced swim test, see e.g.: Porsolt R D, Anton G, Blavet N and Jalfre M, 1978, Behavioural despair in rats: A new model sensitive to antidepressant treatments, *Eur J Pharmacol* 1978, 47:379–391 and the differential reinforcement of low rates of responding model in rats, see e.g.: McGuire P S and Seiden L S, The effects of tricyclic antidepressants on performance under a differential-reinforcement-of-low-rate schedule in rats, *J Pharmacol Exp Ther* 1980, 214: 635–641).

At higher doses also dopamine antagonist-like effects were observed (antagonism of apomorphine-induced climbing behaviour in mice, (A), e.g.: Costall B, Naylor R J and Nohria V, Differential actions of typical and atypical agents on two behavioural effects of apomorphine in the mouse, (B), *Brit J Pharmacol* 1978, 63: 381–382; suppression of locomotor activity, e.g.: File S E and Hyde JR G, A test of anxiety that distinguishes between the actions of benzodiazepines and those of other minor tranquillisers or stimulants, *Pharmacol Biochem Behav* 1979, 11: 65–79 and inhibition of conditioned avoidance response in rats, e.g.: Van der Heyden J A M, Bradford L D, A rapidly acquired one-way conditioned avoidance procedure in rats as a primary screening test for antipsychotics: influence of shock intensity on avoidance performance, *Behav Brain Res* 1988, 31: 61–67). The first two activities, A and B have previously been reported for partial dopamine $D_2$-receptor agonists by Mewshaw et.al, *Bioorg. Med. Chem. Lett.* 8 (1998) 2675.

The compounds are likely to be of value in the treatment of affections or diseases of the central nervous system, caused by disturbances of the dopaminergic and/or serotonergic systems, for example: anxiety disorders (including e.g. generalised anxiety. Panic, Obsessive compulsive disorder), depression, autism, schizophrenia, Parkinson's disease, disturbances of cognition and memory.

Suitable acids with which the compounds of the invention can form acceptable acid addition salts are for example hydrochloric acid, sulphuric acid, phosphoric acid, nitric acid, and organic acids such as citric acid, fumaric add, maleic acid, tartaric acid, acetic acid, benzoic acid, p-toluene sulphonic acid, methane sulphonic acid and naphtalene sulphonic acid.

Prodrugs are derivatives of the compounds having formula (I) wherein $R_4$ is a group which is easily removed after administration. Suitable prodrugs for example are compounds wherein N—$R_4$ is one of the following groups: amidine, enamine, a Mannich base, a hydroxy-methylene derivative, an O-(acyloxymethylene carbamate) derivative, carbamate or enaminone.

The compounds and the salts thereof can be brought into forms for administration by means of usual processes using auxiliary substances such as liquid and solid carrier materials.

The compounds of the invention can be prepared according to methods known for the synthesis of analogous compounds.

Compounds having formula (I) can be obtained by reacting the corresponding compound wherein Q is hydrogen with a compound Q-Hal, wherein Q is methyl (optionally fluorinated) ethyl, or (optionally fluorinated) cyclopropylmethyl and Hal is halogen, preferably iodine. This reaction can be carried out in a solvent such as acetonitrile in the presence of a base, for example ethyl-diisopropylamine or triethylamine.

The starting compounds wherein Q is hydrogen and . . . Z is —N are known or can be obtained as described in EP 0189612. Startng compounds wherein Q is hydrogen and . . . Z is =$CH_2$ can be obtained as described below.

The compounds of the invention wherein . . . Z is —N, can also be obtained by reacting a compound having formula (II)

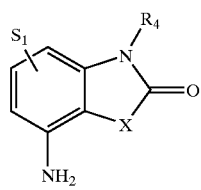

(II)

with a compound of the formula (III)

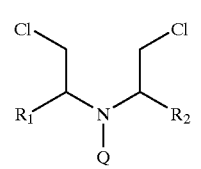

(III)

in which formulae the symbols have the above meanings. This reaction can be carried out in an organic solvent such as chlorobenzene.

The compounds having formula (I) wherein . . . Z represents =C can also be obtained according to the method indicated in the following scheme:

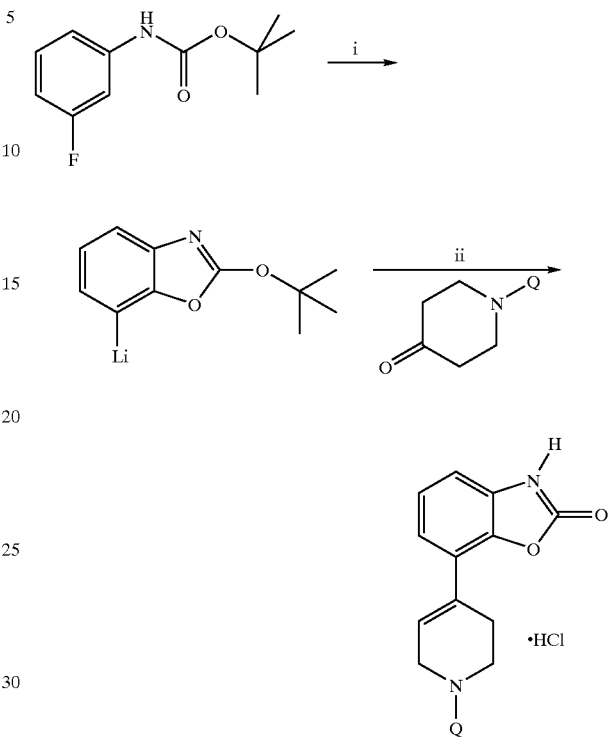

The startng compound for step (i) can be obtained according to the procedure described in J. Org. Chem. 45, (1980), 4789, and step (i) itself can be carried out as described in J. Org. Chem., 47, (1982), 2804.

Step (ii) is carried out in a manner known for this type of chemical reactions, and is elucidated in Example 3.

The invention will be illustrated in the following Examples:

EXAMPLE 1

1.28 g (5 mmol) of I-H.HCl was suspended in 25 ml of acetonitrile and 0.34 ml (4.4 mmol) of ethyliodide together with 5 ml of di-isopropyl ethyl amine were added. The resulting reaction mixture was stirred and refluxed for 18 hrs under a nitrogen atmosphere. The reaction mixture was allowed to reach room temperature after which a small quantity of $SiO_2$ was added. The resulting suspension was concentrated in vacuo leaving a powder which was put on top of a chromatography column after which a chromatography run was done ($SiO_2$, eluent $CH_2Cl_2$/MeOH 95/5) yielding 0.55 g of a white solid. The latter was crystallized from EtOAc/EtOH (ca. 1/1) to which 1.1 equivalent of 1 M HCl/EtOH was added. The crystals were collected by filtration, washing with respectively EtOAc and di-ethyl ether yielded after drying 0.5 g (42%) of the desired HCl salt of the compound wherein $S_1$, $R_1$, $R_2$ and $R_4$ are hydrogen, X is oxygen, . . . Z is —N, and Q is ethyl, mp 280–2° C. (dec.).

EXAMPLE 2

6.0 g (40 mmol) of the compound having formula (II) (wherein $S_1$ and $R_4$ are hydrogen and X is oxygen) was dissolved in 150 ml of chlorobenzene after which 8.47 g (44 mmol) of N-methyl-bis(chloro-ethyl)amine monohydrochloride was added. The resulting reaction mixture was stirred and brought to reflux. The water present in the starting materials was separated by means of a Dean-Stark device. After 44 hrs solid material had formed and the reaction mixture was allowed to reach room temperature. The liquid was separated, the residue was washed with toluene after which it was refluxed in ethanol. After cooling the solid material was filtered and subsequently purified by flash column chromatography (SiO$_2$, eluent: CH$_2$Cl$_2$/MeOH/NH$_4$OH=97/2.5/0.5). This procedure yielded 4.5 g of solid material which was dissolved in 96% EtOH (ca. 300 ml) after which, while stirring, 2 equivalents of 1M HCl/MeOH were added. Crystallizaton started and eventually, after filtration and drying, 4.15 g (38%) of the hydrochloride of the desired compound wherein S$_1$, R$_1$, R$_2$ and R$_4$ are hydrogen, X is oxygen, . . . Z is —N, and Q is methyl could be isolated, mp 301.5–302.5° C.

EXAMPLE 3

Under an inert atmosphere, 16.5 g (78.2 mmol) of N-(tert.butyloxycarbonyl)-meta-fluoroaniline were dissolved in 230 ml of dry tetrahydrofuran (THF) after which the solution was cooled to −75° C. (dry ice, acetone). While stirring a commercially available solution of 1.5 M tert.butyl-lithium in heptane (ca. 156 mmol, 2 molequivalents) was added slowly, after which the reaction mixture was stirred for 0.5 hr at −70° C., and subsequently for an additional 2 hrs at −25° C. Again the reaction mixture was brought to −75° C. and a solution of 9.6 ml of N-methylpiperidone (78.2 mmol, 1 molequivalent) in ca. 25 ml of dry THF. The reaction mixture was allowed to reach room temperature and stirred for an additional 16 hrs. Subsequently a solution of 1.5 ml (83 mmol) of H$_2$O in 50 ml of MeOH was added slowly to the reaction mixture, after which 100 ml of SiO$_2$ was added. The suspension was evaporated to dryness after which the resulting powdery residu was put on top of a chromatography column after which a "flash"-chromatography run was done (SiO$_2$ first eluent: EtOAc, second eluent: MeOH/EtOAc/tri-ethylamine 15/85/1) yielding 12.4 g of a dark yellow oil.

While stirring, 4.7 g (ca. 15.5 mmol) of the obtained product were dissolved in 100 ml of dioxan after which 100 ml of concentrated HCl was added, the resulting mixture was refluxed for 1 hr. The reaction mixture was allowed to reach room temperature after which it was concentrated in vacuo, yielding a solid residu. The residu was suspended and stirred in i-propanol after which the solid material was filtered and subsequently washed with respectively EtOAc, di-ethyl ether and hexane. After drying 3.1 g of residu was left of which 1.5 g was suspended in EtOH, the latter suspension being refluxed for 1 hr. The mixture was allowed to reach room temperature after which it was filtered, yielding a residu which was washed with absolute EtOH and di(i-propyl) ether respectively. After drying 1.1 g (53%) of the desired compound wherein S$_1$, R$_1$, R$_2$ and R$_4$ are hydrogen, X is oxygen, . . . Z is =C, and Q is methyl was obtained, $^1$H-NMR(400 MHz, D$_2$O):

$^1$H-NMR(400 MHz, D$_2$O): δ 2.96 (broad, 2H, H-5); 3.04 (s, 3H, H-7); 3.3–4.3 (broad, 4H, H-2, H-6); 6.4 (m, 1H, H-3); 7.14 (d, 1H, H-8 or H-10, J=8 Hz); 72 (d, 1H, H-10 or H8, J=8 Hz); 7.26 (t, 1H, H-9, J=8 Hz), using the numbering as indicated in the following formula:

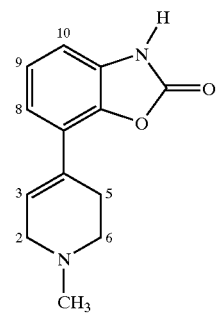

What is claimed is:
1. A compound having formula (I)

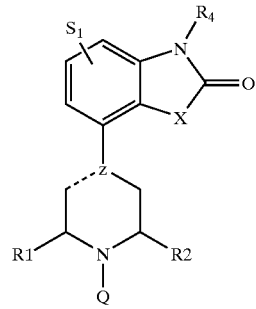

wherein

S$_1$ is hydrogen, halogen, alkyl (1–3C), CN, CF$_3$, OCF3, SCF3, alkoxy (1–3C), amino or mono- or dialkyl (1–3C) substituted amino, or hydroxy, X represents NR$_3$, S, CH$_2$ or O, SO or SO$_2$, wherein R$_3$ is H or alkyl (1–3C), . . . Z represents =C or —N, R$_1$ and R$_2$ independently represent H or alkyl (1–3C), R$_4$ is hydrogen or alkyl (1–3C), Q is methyl, ethyl, ethyl substituted with one or more fluorine atoms, or cyclopropylmethyl optionally substituted with one or more fluorine atoms, with the proviso that when S$_1$, R$_1$, R$_2$ and R$_4$ are hydrogen, . . . Z is =C and Q is ethyl, X cannot represent CH$_2$, and salts and prodrugs thereof, wherein the prodrugs are chosen from compounds having the formula (I) in which N—R$_4$ is an amidine, enamine, Mannich base, hydroxy-methylene derivative, O-(acyloxymethylene carbamate) derivative, carbamate, or enaminone.

2. The compound as claimed in claim 1, wherein S$_1$, R$_1$, R$_2$ and R$_4$ are hydrogen, X represents oxygen, Q is methyl or ethyl and . . . Z has the meaning given in claim 1.

3. The compound as claimed in claim 2, wherein . . . Z represents —N.

4. The compound as claimed in claim 3 wherein Q is methyl.

5. The compound as claimed in claim 1, wherein S$_1$, R$_1$, R$_2$ and R$_4$ are hydrogen, X represents oxygen, Q is methyl, ethyl, or cyclopropylmethyl.

6. The compound as claimed in claim 5 wherein Q is methyl.

7. Method for the preparation of a compound as claimed in claim 1 comprising reacting a compound having formula (I) wherein Q is hydrogen, with a compound of the formula Q-Hal wherein Q is methyl, optionally fluorinated ethyl, or optionally fluorinated cyclopropylmethyl, and Hal is halogen, to yield the compound as claimed in claim 1.

8. Method for the preparation of a compound having formula (I) as claimed in claim 1 wherein . . . Z represents —N comprising reacting a compound having formula (II)

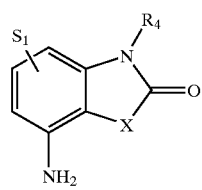
(II)

with a compound having formula (III)

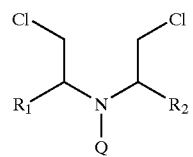
(III)

in which formulae the symbols have the meanings given in claim 1, to yield the compound having formula (I).

9. Method for the preparation of a compound having formula (I) as claimed in claim 1 wherein . . . Z represents =C, comprising reacting a compound having formula (IV)

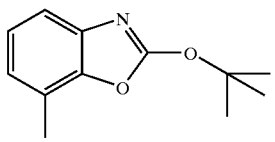
(IV)

with a piperidone derivative which is optionally $R_1$ and/or $R_2$ substituted, and carries a group Q, followed by dehydration and deprotection, to yield the compound having formula (I).

10. A pharmaceutical composition comprising an effective amount of at least one compound having formula (I) as claimed in claim 1, and at least one auxiliary substance.

11. Method of preparing a pharmaceutical composition, comprising bringing at least one compound having formula (I) as claimed in claim 1 and at least one auxiliary substance into a form suitable for administration to an animal patient.

12. A method of treating at least one CNS disorder, comprising administering at least one compound having formula (I) as claimed in claim 1 to an animal patient in need thereof in an amount effective for said treating, wherein the at least one CNS disorder is chosen from anxiety disorders, generalized anxiety, panic, obsessive compulsive disorder, depression, autism, schizophrenia, Parkinson's disease, and disturbances of cognition and memory.

13. A method of treating anxiety, depression, or a combination of anxiety and depression, comprising administering at least one compound having formula (I) as claimed in claim 1 to an animal patient in need thereof in an amount effective for said treating.

* * * * *